United States Patent [19]

Meuli et al.

[11] Patent Number: 4,675,016

[45] Date of Patent: Jun. 23, 1987

[54] METHOD FOR ADHERING CURVED TENSIONED ELASTIC STRIPS TO A GATHERABLE BASE MATERIAL AND THE ARTICLE PRODUCED

[75] Inventors: Michael G. Meuli, Menasha; Gary H. Knauf, Neenah, both of Wis.

[73] Assignee: Kimberly-Clark Corporation, Neenah, Wis.

[21] Appl. No.: 789,986

[22] Filed: Oct. 22, 1985

[51] Int. Cl.$^4$ .................. A61F 13/16; B32B 31/08
[52] U.S. Cl. .................. 604/385 A; 156/164; 156/229; 428/152
[58] Field of Search ............... 156/161, 163, 164, 176, 156/177, 178, 229, 301, 302, 308.2; 428/152, 176, 184, 230, 231; 604/385.2; 2/78 C, 76, 270; 428/114

[56] References Cited

U.S. PATENT DOCUMENTS

| | | | |
|---|---|---|---|
| 3,616,123 | 10/1971 | Reynolds et al. | 156/229 X |
| 3,904,467 | 9/1975 | Srail | 156/229 |
| 4,023,571 | 5/1977 | Comerford et al. | 604/385.1 |
| 4,259,220 | 3/1981 | Bunnelle et al. | 260/27 |
| 4,418,123 | 11/1983 | Bunnelle et al. | 428/517 |
| 4,556,596 | 12/1985 | Meuli | 428/152 |

Primary Examiner—Michael W. Ball
Assistant Examiner—Geoffrey L. Knable
Attorney, Agent, or Firm—Paul Yee

[57] ABSTRACT

A method for applying one or more curved composite elastic strips to a gatherable base material to elasticize portions of the base material comprises elongating a first strip of elastic material and joining a second strip of less elongated material to the elongated first strip in a longitudinally extending and laterally off-set relationship thereto to form a tensioned composite strip of elastic material. The second strip of material is sufficiently flexible in the plane of the composite strip and is sufficiently resistant to compression so that, upon release of the tensioning forces, the composite strip will curve laterally, i.e., in its own plane. The tensioned composite strip is adhered to the base material and in one mode of operation the tensioned forces are released only after adhering the composite strip to the base material. In such case, the base material is displaced somewhat by curving of the tensioned composite strip and may be pleated or otherwise rendered more readily displaceable. The resulting article comprises one having curved elasticized strips adhered thereto to elasticize portions thereof.

26 Claims, 9 Drawing Figures

4,675,016

METHOD FOR ADHERING CURVED TENSIONED ELASTIC STRIPS TO A GATHERABLE BASE MATERIAL AND THE ARTICLE PRODUCED

BACKGROUND OF THE INVENTION

1. Field of the Invention

The present invention is concerned with a method for adhering curved tensioned strips of elastic material to a gatherable base material in order to elasticize portions of the base material, and is also concerned with the elasticized article thereby obtained. The invention finds particular application in elasticizing garments, in particular in elasticizing disposable incontinence control garments, for example, disposable diapers. The manufacture of such articles is usually carried out by joining continuous moving webs of material to form a composite web which is then cut transversely to form the individual articles. It is often desired to elasticize portions of the garments, such as the leg cut-out portions of disposable diapers, in order to provide a snug fit of the diaper about the wearer's legs to aid in controlling or preventing leakage. It is a common expedient in the art to apply bands of elastic material under tension to a moving web or webs of material, utilizing an adhesive, electronic welding, mechanical stitching or any suitable means to secure the tensioned elastic band to the web. Because the elastic band is glued or otherwise secured to the web while held in a tensioned, elongated condition, upon cutting of the web into individual articles the tensioned, elongated elastic bands relax to form elasticized gathers in the flexible material. Generally, any suitable elastic material comprising a suitable rubber, synthetic organic polymeric material or composite material may be utilized as the elastic band.

2. Description of the Related Art

A particularly useful material for the elastic bands would be one which is both elastic and self-adhering to the gatherable base material which is to be elasticized. Such self-adhering elastic materials are known and obviate the need for separate gluing or other steps to secure the elastic bands to the gatherable base material. For example, U.S. Pat. No. 4,259,220 and related U.S. Pat. No. 4,418,123, respectively disclose (1) a viscoelastic, hot melt, pressure sensitive adhesive which can be extruded to form a tape which is both pressure sensitive adhesive and elastic, and (2) a method for imparting elastic properties to a flexible substrate by contacting a surface of the substrate with the specified self-adhering elastic material. The disclosure of each of U.S. Pat. No. 4,259,220, issued Mar. 31, 1981 to William L. Bunnelle et al, and U.S. Pat. No. 4,418,123, issued Nov. 29, 1983 to William L. Bunnelle et al, is incorporated by reference herein.

U.S. Pat. No. 4,023,571 discloses the manufacture of an absorbent undergarment utilizing an absorbent first layer having the property of elastic recovery, which is described as the capability of being elongated under tensile stress and at least partially recovering from the elongation upon release of the tensile stress. A relatively inelastic second layer or member (26 in FIG. 3) is adhered to the first layer (16 in FIG. 3) in laterally coextensive and mutally centered relationship while the first member is held longitudinally under tension. Upon release of the tension the flat laminate gradually acquires an arcuate shape (FIGS. 4 and 5 and items 10, 10' in FIG. 6) as the elastic recovery forces of absorbent layer 26 are resisted by the relatively inelastic second layer 28. See Column 6, lines 3-27. The arcuate shape results from bowing of the laminated layers out of their original flat plane in a direction perpendicular thereto.

The application of bands of elastic material under tension to a moving web of material, as is practiced in the manufacture of items such as disposable diapers, presents difficulties including those which arise from the fact that the webs of material are usually traveling at high rates of speed, for example, from 500 to 600 feet per minute. These high web speeds are required for efficient manufacture but make it difficult to adhere elastic strips to the moving web, particularly if it is sought to do so in other than a straight linear configuration of the elastic strips. Another difficulty is that self-adhering elastic materials of the type described in the aforementioned Bunnelle et al U.S. patents is that, at least with respect to certain base materials such as the polyolefin sheet materials normally used in disposable diaper manufacture, the greater the degree to which the self-adhering elastic materials are elongated when applied to the base material, the less adherent to the base material do the elastic materials become. In other words, the greater the degree of elongation to which the self-adhering elastic materials are subjected upon being adhered to the polyolefin base material, the more is the self-adhering power of the elastic material reduced. One solution to the latter problem is set forth in co-pending patent application Ser. No. 676,920 (now U.S. Pat. No. 4,556,596) of Michael G. Meuli, filed Nov. 30, 1984, and entitled "Method for Adhering Tensioned Elastic Strips to a Gatherable Base Material", in which the tensioned strip of self-adhering elastic material is secured to the moving web of base material by a second, less or untensioned strip of self-adhering elastic material.

SUMMARY OF THE INVENTION

In accordance with the present invention there is provided a method of adhering one or more curved composite elastic strips to a gatherable base material, which may be a moving continuous web of material, to elasticize at least selected portions of the base material, the method comprising: applying tensioned forces to a first strip of elastic material to elongate it; joining a second strip of less-elongated material to the elongated first strip in longitudinally extending, laterally off-set relationship thereto to form a tensioned composite strip of elastic material, the second strip being sufficiently laterally flexible and sufficiently resistant to compression to cause the composite strip to laterally curve upon release of the tensioning forces; releasing the tensioning forces on the composite strip whereby to allow it to laterally curve; and adhering the composite strip to the base material.

One aspect of the invention includes adhering the tensioned composite strip to the base material before releasing the tensioning forces on the composite strip to allow it to curve laterally by displacing base material adjacent thereto.

Other aspects of the invention include one or more of the following: applying the second strip to the first strip in a laterally off-set relation thereto such that not more than about three-quarters, preferably about one-fifth to not more than three-fifths, of the width of the first strip is overlaid by the second strip; and first strip may be a self-adhering elastic material; the first and second strips may comprise the same self-adhering elastic material;

tensioning the first strip to impose thereon from about 100% to 400% elongation; the first strip may comprise a self-adhering elastic material comprising (a) a block copolymeric material comprising at least one substantially amorphous, rubbery polymeric midblock and at least one glassy poly(vinylarene) endblock, (b) a midblock associating resin, and (c) an endblock associating resin; the gatherable base material may be a polyolefin, e.g., polypropylene; the first and second strips may comprise self-adhering elastic material and the tensioned composite strip may be adhered to the base material by joining the second strip to the base material.

Still another aspect of the invention includes the first and second strips being comprised of self-adhering elastic materials of the type whose strength of adherence to the base material is inversely proportional to the degree of elongation imposed on the strip during adherence to the base material.

In accordance with other aspects, the invention may include one or more of the following: the preliminary step of forming strips of self-adhering elastic material in situ from at least one mass of source material and employing the freshly formed strips in the method; transversely cutting the web into discrete articles containing thereon one or more segments of the composite strip thereby releasing the tensioning forces of the one or more segments of composite strips; and enhancing displaceability of the base material by configuring one or more portions thereof adjacent composite strips adhered thereto to free such portions for movement by the laterally curving composite strips.

Articles are provided in accordance with the invention, including garments such as disposable diapers, made by the above-described methods.

DETAILED DESCRIPTION OF THE PREFERRED EMBODIMENTS

Figure 1:
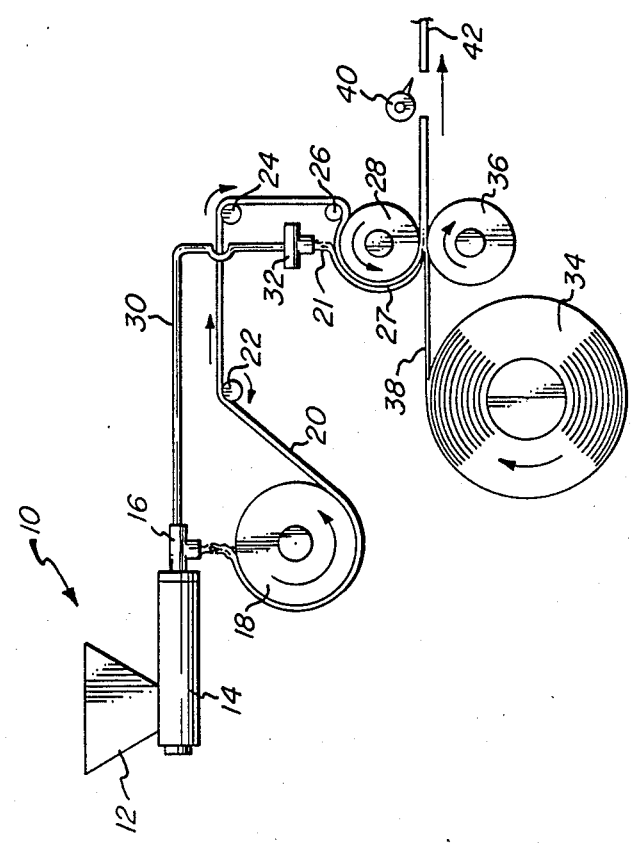
FIG. 1 is a schematic view in elevation illustrating one embodiment of carrying out the method of the present invention.

FIG. 1 shows in schematic elevation view a method of carrying out one embodiment of the invention wherein an extruder generally indicated at 10 comprises a feed hopper 12 and a screw housing 14 to which is attached an extruder nozzle 16 which is preferably of a type which will produce a relatively wide, flat ribbon of extruded material. Such an extruder nozzle is described, for example, in U.S. Pat. No. 4,389,181 of R. H. Frick, issued June 21, 1983, the disclosure of which is incorporated by reference herein. A suitable material, for example, one as described in the Bunnelle et al patents incorporated by reference herein, is introduced into hopper 12 and melted to provide a softened plastic extrudable mass of source material from which the strips are formed. A wide flat ribbon of extruded material is deposited from extruder nozzle 16 onto a chill roller 18 which comprises a conventional cooled roller rotating in the direction indicated by the arrow associated therewith and onto which the extruded ribbon is deposited for cooling and setting. Chill roller 18 may be maintained at, say, 0° C. (32° F.) in order to chill a material of the type described in the aforementioned Bunnelle et al U.S. Pat. Nos. 4,259,220 and 4,418,123. A plurality of extruders or a plurality of extruder nozzles 16 may be arranged to deposit a plurality of extruded ribbons of material onto chill roller 18, as will be appreciated by those skilled in the art. In any event, one or more first strips 20 of chilled, extruded material are passed to a roller 22 which is rotating in the direction indicated by its associated arrow, and which cooperates with rollers 24 and 26 to direct and transport first strip or strips 20 onto a driven roller 28 which may, but need not necessarily, be a chill roller. Roller 28 rotates with a greater peripheral speed than chill roller 18, whereby the first strip or strips 20 are tensioned and elongated to a desired degree.

A heated conduit 30 is connected in fluid flow communication with extruder nozzle 16 and transports a portion of the fluid mass extruded from screw housing 14 to a remote extruder nozzle 32. Remote extruder nozzle 32 may extrude a wide, flat ribbon-like second strip 21 similar to but narrower than that extruded from extruder nozzle 16. Alternatively, second strip 21 may be as wide as or wider than first strip 20. In any event, the material extruded from remote extruder nozzle 32 or a plurality of remote extruder nozzles 32 is deposited upon the extruded strip or strips 21 in longitudinally extending, parallel but laterally off-set overlying relationship as illustrated in FIGS. 3 and 3A and 5 and 5A as described more fully below. Consequently, there is formed on joining roller 28 a plurality of first strips 20 of self-adhering elastic material extruded from extruder nozzle 16 and having thereon one or more overlying, laterally off-set strips 21 of self-adhering elastic material extruded from extruder nozzle 32. As the first strips 20 are maintained under tension by the rollers 22, 24, 26 and 28 and thereby elongated while the second strips 21 are deposited thereon, there are formed one or more tensioned composite strips 27 comprised of first strips 20 and second strips 21 of self-adhering elastic material.

A roll 34 of gatherable base material, such as a thin, relatively wide polyolefin material is unwound in the direction indicated by its associated arrow to provide a moving continuous web of gatherable base material 38. As used herein and in the claims, a "gatherable" material is one which, when a tensioned and thereby elongated elastic member is attached to it will, upon release of the tensioning force, be gathered into pleats or gathers upon contraction of the elastic member. The size, strength and elasticity of a given elastic member, of course, determines whether or not it can gather a given base material so, to that extent, the term gatherable is relative to the elastic member or members applied thereto. For example, web 38 may comprise a web of polyolefin material such as polypropylene which is from ½ to 2 mils thick and from 10 to 15 inches (25.4 to 38.1 cm) wide. Web 38 is brought into contact with the tensioned composite strips 27 of self-adhering elastic material in the nip formed between joining roller 28 and pressure roller 36 whereby the tensioned composite strips 27 are joined with and self-adhered to the continuous moving web 38.

Figure 3:
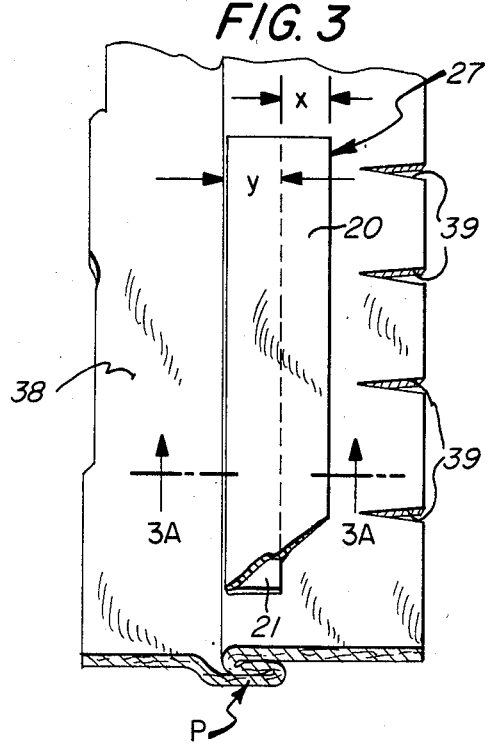
FIGS. 3 and 3A are, respectively, plan and end views in section of composite elastic strips in accordance with specific embodiments of the invention adhered to a gatherable base material.
Figure 4:
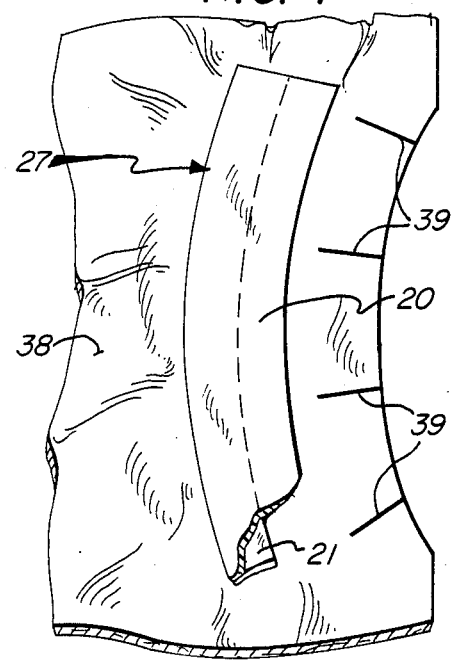
FIG. 4 is a plan view of the embodiment corresponding to FIG. 3 but after release of tensioning forces on the composite strip to allow the composite strip to curve laterally.
Figure 3A:
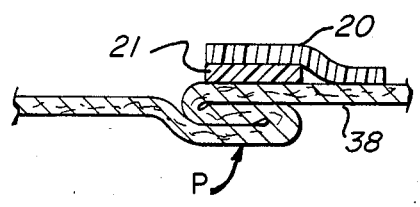
Figure 5:
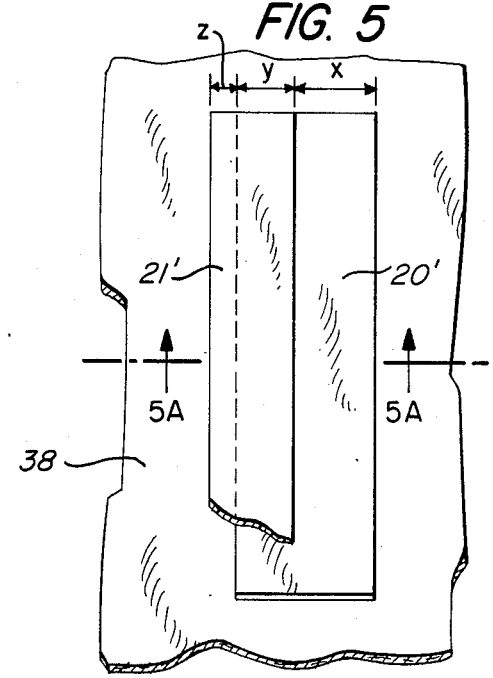
FIGS. 5 and 5A are, respectively, plan end views in section generally corresponding to FIGS. 3 and 3A but of another embodiment of the invention.
Figure 5A:
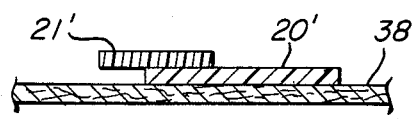
Figure 6:
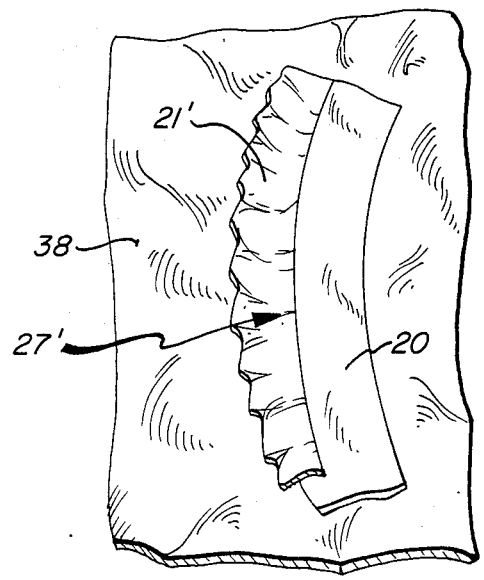
FIG. 6 is a plan view of the embodiment of FIG. 5 but after release of tensioning forces on the composite strip to allow the composite strip to curve laterally.

A cutter 40 may be utilized to cut the web of gatherable material 38 into a plurality of discrete articles 42. As the tension of moving continuous web 38 is released by the cutting, the tensioning forces applied to first strip 20 are released which causes the composite strip 27 to curve in its plane because the contraction of first strip 20 is resisted by laterally off-set second strip 21. Second strip 21, which is firmly adhered to first strip 20, although resistant to compression is sufficiently flexible in the plane in which the composite strip lies to curve laterally as illustrated in FIG. 4 upon release of the tensioning force from the composite strip 27. As used herein and in the claims, reference to either strip or to the composite strip as being able to "curve laterally" or to be sufficiently "laterally flexible" to curve, or to "lateral curving" of such strips, or terms of like import means that the strip or composite strip curves primarily in its own plane which, for purposes of this definition, is deemed to have a thickness equal to that of the strip or composite strip. For example, with respect to FIGS. 3, 4, 5 and 6, the plane of the composite strip is approximated by the plane of the paper on which the Figures are drawn and lateral curving as illustrated in FIGS. 4 and 6 takes place within the plane of the composite strip (the plane of the paper) as distinguished from the case of the strip bowing perpendicularly above or below the plane of the strip, i.e., above or below the plane of the paper on which the drawing is made. As shown in FIG. 3, composite strip 27 is applied to web 38 which second strip 21 positioned between web 38 and first strip 20, as best seen in FIG. 3A. The respective thicknesses of web 38 and strips 20 and 21 in FIG. 3A and strips 20′ and 21′ in FIG. 5A are exaggerated for clarity of illustration as is the thickness of pleat P formed in web 38. First strip 20 and second strip 21 are usually considerably thinner relative to their width than is shown in FIG. 3A so that first strip 20 lies more nearly flat upon web 38 than suggested in FIG. 3A. In any event, tensioned composite strip 27 is still maintained under tension in the known manner until upon cutting of web 38 into discrete articles 42, tensioning forces acting on composite strip 27 are released and first strip 20, which was elongated prior to adherence to second strip 21 and web 38, tends to relax and contract to approximately its length prior to elongation. However, second strip 21, being resistant to compression but flexible in the plane of composite strip 27, resists contraction by first strip 20 resulting in lateral curving of composite strip 27 as shown in FIG. 4. The degree of curvature sustained by composite strip 27 upon release of the tensioning forces acting thereon depends upon the elastic strength and degree of elongation of first strip 20 relative to any elongation of second strip 21, the resistance to compression and lateral flexibility of second strip 21 and the amount of lateral off-set of second strip 21 relative to first strip 20. For example, if second strip 21 were centered along the longitudinal axis of first strip 20 no lateral curvature would occur upon release of the tensioning force although bowing of the composite strip would be expected. However, with second strip 21 laterally off-set relative to the longitudinal center line of first strip 20, the resistance of second strip 21 to contraction of first strip 20 upon release of the tensioning force acting thereon will cause the lateral curvature illustrated in FIG. 4. Other things being equal, the greater the degree of off-set the greater will be the degree of lateral curvature attained. The composite strip will curve laterally in a direction such that the side edge thereof which is remote from second strip 21 will assume a concave configuration and the side edge adjacent to second strip 21 will assume a convex configuration, as shown in FIGS. 4 and 6. Preferably, although not necessarily, second strip 21 is laterally off-set sufficiently so that not more than three-quarters, say, one-half or less, of the width of first strip 20 is overlaid by second strip 21. With reference to FIGS. 3 and 5, for example, this means that, preferably, width x is at least one-third as wide as width y.

When composite strip 27 is adhered to web 38 prior to release of the tensioning force acting thereon, composite strip 27 must, upon laterally curving, displace the material of web 38 lying adjacent thereto, the web 38 tending to resist the curvature of composite web 27. Base material 38 is usually quite thin (e.g., 1 to 2 mils thick) and is gatherable and therefore generally offers little resistance to lateral curvature of composite strip 27, tending to be stretched, gathered or otherwise displaced. However, in order to enhance such displaceability of the base material of web 38, a pleat P may be formed in web 38 as illustrated in FIGS. 3 and 3A to provide some play in web 38 thereby eliminating or reducing resistance offered by web 38 to lateral curving of composite strip 27. Alternatively, or in addition, a series of V-shaped notches 39 may be formed along an edge of web 38 adjacent the side of composite strip 27 which will attain a concave configuration upon curving thereof. Notches 39 cooperate with pleat P in the illustrated embodiment to eliminate or reduce the resistance of the material of web 38 to lateral curving of composite strip 27.

FIG. 5 illustrates another embodiment of the invention wherein a first strip 20′ is adhered to the material of web 38 and a second strip 21′ is adhered to first strip 20′ resulting in a configuration as illustrated in end view in FIG. 5A in which second strip 21′ is adhered to first strip 20′ with a lateral width z (FIG. 5) extending beyond the convex curving edge of first strip 20′. Further, in this embodiment second strip 21′ is adhered to first strip 20′ on the side thereof opposite to the material of web 38. Upon release of the tensioning forces acting on composite strip 27′, the free lateral edge segment (width z) of second strip 21′ tends to pucker as shown in FIG. 6, the portion of second strip 21′ which is adhered to first strip 20′ nonetheless providing the desired lateral curving as seen in FIG. 6.

Generally, as mentioned above, the degree of curvature attained can be increased by increasing the difference in initial elongation of the first and second strips and by increasing the degree of lateral off-set of the second strip relative to the first strip. As used herein and in the claims, reference to adhering the second strip in a position which is "laterally off-set" relative to the first strip means that the second strip is adhered in overlying relationship to the first strip with the two strips being in more or less parallel alignment with their respective longitudinal axes off-set so that a longitudinally extending segment of the first strip is left uncovered by the second strip. Both the first and second strips may be adhered under tension, with the first strip being elongated to a greater degree than the second strip when the two strips are joined together. Alternatively, the first strip may be tensioned and elongated and the second strip not elongated at all when the two strips are joined together. In any case, when the composite strip 27 is adhered to a base material such as web 38 and the tensioning forces acting on the composite strip 27 released, there is provided a laterally curved elasticized gathered portion of the resultant article 42. It will be noted that the second strips 21 are sandwiched between the surface of web 38 and the first strip 20 in the embodiments of FIGS. 3, 3A and 4. Since the second strips of material 21 are untensioned or less tensioned, when self-adhering materials of the type described in the aforesaid Bunnelle et al patents are used as the elastic strips, strips 21 retain a relatively high degree of self-adherence to, e.g., polypropylene, material of flexible web 38. Therefore, even if first strips 20 are made of the material of the aforesaid Bunnelle et al patents and are elongated to a degree in which they are rendered significantly less adherent to the material of web 38 by virtue of their tensioned, elongated state, untensioned strips 21 of the same material provide enhanced adherence of the composite strips 27 to web 38.

Figure 2:
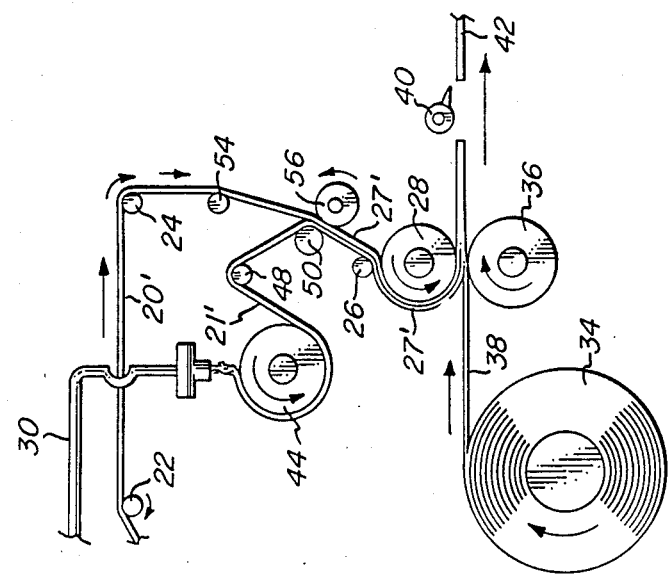
FIG. 2 is a partial schematic view in elevation of an alternate embodiment of carrying out the method of the invention.

FIG. 1 illustrates a method in which second strips 21 are untensioned. Referring now to FIG. 2, there is shown an alternate embodiment of making the composite strips of the invention in which both first strips 20' and second strips 21' may be placed under tension and elongated with, however, first strips 20' being elongated to a greater degree than second strips 21'. In the FIG. 2 embodiment, extruder 10, chill roller 18 and extruder nozzle 16 are identical to those of the FIG. 1 embodiment and thus have been omitted to avoid repetition, and other parts in the FIG. 2 embodiment which are identical to those of the FIG. 1 embodiment are identically numbered. Heated conduit 30 is identically connected in fluid flow communication between extruder nozzle 16 (not shown in FIG. 2) and remote extruder nozzle 32, which in this case deposits its extruded strips onto a second chill roller 44 to provide one or more second strips 21' of extruded self-adhering elastic material. Roller 48 rotates in the direction opposite to that of second chill roller 44 and has a higher peripheral speed than does chill roller 44. Second strips 21' are tensioned and elongated to a desired degree which is less than that to which first strips 20' are elongated. The degree of tensioning and elongation of second strips 21' is maintained by rollers 50 and 26.

First strips 20' obtained from chill roller 18 (not shown in FIG. 2) are tensioned and elongated by driven roller 28 and maintained under such tension and elongation, which is greater than that of second strips 21'. The first strips 20' and second strips 21' of self-adhering elastic material are joined together in parallel overlying relationship by the nip formed between roller 50 and pressure roller 56 to form a tensioned composite strip 27' which is wound about joining roller 28 which, as in the FIG. 1 embodiment, cooperates with pressure roller 36 to apply composite tensioned strip 27' to continuous moving web 38. Second strips 21' are sandwiched between first strip 20' and the material of moving continuous web 38. As in the FIG. 1 embodiment, a cutter 40 may be utilized to cut the moving web of flexible material 38 having the tensioned composite strips 27' joined thereto into discrete articles 42.

Generally, an efficient mode of production of elasticized articles utilizing a continuous moving web of a base material comprises applying the tensioned composite strip in a straight linear configuration to the moving web of material and thereafter releasing the tensioning forces to permit the composite strip to laterally curve while displacing portions of the base material adjacent the strip. The base material may be pleated, notched, diamond cut, or otherwise treated to render at least portions of it more readily displaceable thereby reducing or eliminating resistance to curvature of the composite strip afforded by the base material to which the composite strip is adhered. Alternatively, the composite strip may be formed under tension and cut to allow it to laterally curve prior to being affixed to the web of base material. This may be carried out by releasing the tensioning forces on the composite strip, such as by cutting a continuous tensioned composite strip into discrete lengths, and holding the resultant laterally curved lengths on a platen by suitable means, such as vacuum means, mechanical retaining means or a platen surface to which the composite strip will temporarily adhere. The platen holding the curved composite strip may then be brought into contact with a web of base material, e.g., a moving continuous web, and the curved composite strip pressed onto and adhered to the base material by the platen in a manner analogous to a printing operation. For example, one or a plurality of such platens may be mounted for orbiting movement into pressing contact with a continuous moving web thence to a supply station for positioning of another composite strip onto the platen.

Figure 7:
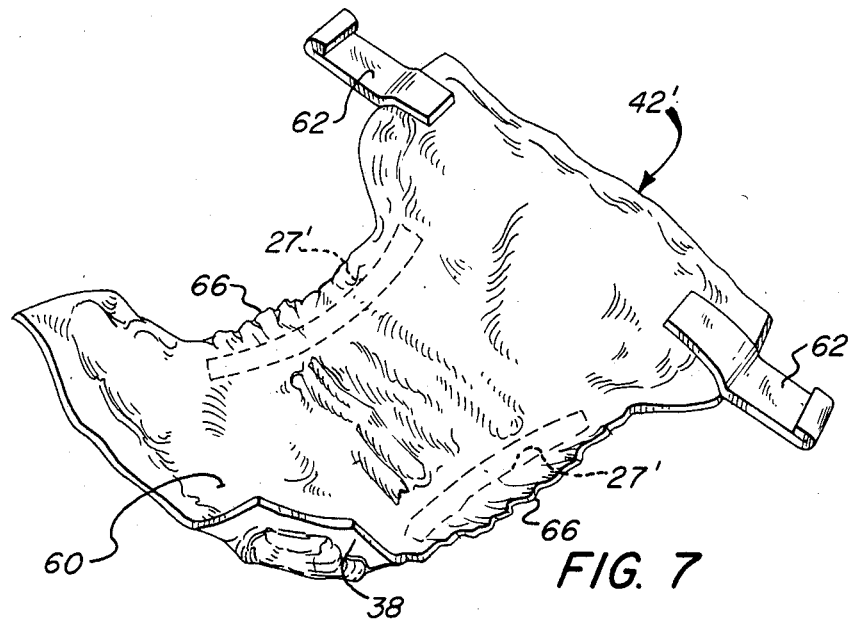
FIG. 7 is a perspective view of an elasticized article made in accordance with the invention and comprising a disposable diaper.

FIG. 7 illustrates an article 42' cut from a moving web of continuous material to which a tensioned composite strip 27' of self-adhering elastic material has been secured. The illustrated article 42' comprises a disposable diaper comprising a thin polypropylene backing sheet 38' cut from a continuous moving web of gatherable base material to which has been joined an intermediate absorbent web of material, not visible in FIG. 7, but whose bulk is indicated by the stretch lines on the overlying cover sheet 60. Those skilled in the art will recognize the conventional overall construction of a disposable diaper in which respective webs of backing sheet 38', an absorbent material (not shown) and cover sheet 60 are joined in a three-ply layer continuous web which is cut transversely to provide a finished disposable diaper 42'. Conventional adhesive strips 62 are applied for fastening the folded diaper upon the wearer. Composite self-adhering elastic strips 27' of the invention are indicated in dotted lines adjacent the leg cut-outs 66 of diaper 42' and are seen to provide elasticized gathers in the leg cut-out areas.

Although the first strip of the composite elastic strip may comprise any suitable elastic material, at least the first strip and, preferably, both the first and second strips, are made of a self-adhering elastic material, and most preferably, the second strip is made of the identical material from which the first strip is made. However, it is not necessary that either strip comprise a self-adhering elastic material. The tensioned composite strip may comprise any suitable elastic material which may be secured to the gatherable base material in any suitable fashion such as by gluing, stitching, sonic welding or any combination of suitable techniques. As mentioned above, the second strip need not be elastic at all, provided it exhibits the desired characteristics of being sufficiently flexible to allow curvature in the plane of the composite strip and sufficiently resistant to compression to provide the desired degree of curving upon contraction of the first, elastic strip. The term "elastic" as used herein and in the claims has its usual broad meaning and may conveniently be defined as a material which is capable of being elongated at least 100%, i.e., to a length twice its original untensioned length and, upon release of the tensioning force, will contract to within at least 10%, preferably to within at least 5% or less, of its original length.

The following Examples illustrate preparation of laterally curved composite elastic strips in accordance with specific aspects of the invention.

EXAMPLE I

Strips of elastic material were prepared by extruding, from a Brabender extruder, Fullastic resin designated HM 6650 and sold by H. B. Fuller Company of St. Paul, Minn. An extrusion temperature of 190° C. was maintained and first and second strips of the following dimensions were produced by extrusion through appropriately shaped and sized extrusion nozzles.

First strip: 1.3 centimeters wide by 0.05 centimeters thick, as measured in its relaxed, i.e., unstretched, state; and 0.7 centimeters wide by 0.04 centimeters thick, as measured in its stretched state.

Second strip: 1.3 centimeters wide by 0.05 centimeters thick, as measured in its relaxed state.

With reference to FIG. 3, first strip 20 was placed under tensioning forces to elongate it about 270% elongation (an elongated length equal to 270% of the relaxed length of the strip) by mounting the upper end of a 3.25 cm length of the first strip in a clamp from which the first strip dangled vertically and clipping an 800 gm weight to the lower end of the dangling strip. This weight operated to tension and stretch the first strip to a length of 12 cm. With the first strip maintained under this tensioning force, a 10 cm length of a relaxed second strip 21 was clamped hereto under pressure so that the self-adhering strips adhered firmly to each other with the relaxed, untensioned second strip positioned parallel to but laterally off-set from the longitudinal centerline of the first strip to leave uncovered a 0.3 cm wide lateral section of the first strip. The resulting configuration resembled that of FIG. 3 of the drawings, with the dimension x being 0.3 cm wide and dimension y being 0.4 cm wide. After the strips were adhered to one another the 800 gm weight was removed and as the first strip contracted upon release of the tensioning force the contracting resistance offered by the unstretched second strip resulted in the composite strip laterally curving to a C-shaped configuration.

EXAMPLE II

The experiment of Example I was repeated except that a second strip 21', which was 0.6 cm in width and 8.0 cm in length, (as measured in its relaxed state) was utilized. The second strip was adhered to a first strip in a configuration resembling that of FIG. 5 of the drawings, in which x was 0.3 cm wide, y was 0.4 cm wide and z was 0.2 cm wide. The first strip 20' was tensioned to a 270% elongation with a weight and maintained under such elongation while the second strip in untensioned, relaxed condition was adhered thereto. Upon removal of the weight from the resultant composite strip, the strip curved laterally to acquire a C-shaped configuration. The free lateral segment of the second strip (the width z in FIG. 5) showed a puckered configuration as illustrated in FIG. 6 of the drawings.

As used herein and in the claims, the term "self-adhering elastic material" embraces any otherwise suitable material which is both elastic and self-adherent to the gatherable base material to which it is to be adhered. Such materials usually, upon elongation, become less adherent relative to the gatherable base material. As used herein and in the claims, the term "gatherable base material" means any otherwise suitable material which is flexible enough so that upon adhering of a tensioned elongated elastic material thereto, it will conform to the elastic strip upon relaxation thereof sufficiently to form an elasticized portion of the gatherable base material. Such base materials usually are, or can be, rendered sufficiently displaceable to accommodate the desired degree of curving of the composite strip when the latter is affixed thereto in a straight linear configuration. Reference herein and in the claims to "strips" of elastic material is to be understood as including ribbons, bands, strands or other suitable shapes and configurations. Further, all percentage elongation are expressed as a percent of the unelongated or relaxed length of the strip. Thus, 100% elongation means that the untensioned strip has been stretched to twice its relaxed, i.e., untensioned, length. As used herein and in the claims, references to a "less-tensioned" second strip includes one which is untensioned as well as one which is tensioned, but to a percent elongation less than that of the first strip. Similarly, reference to forming the strips "in situ" means that the strips are extruded or otherwise formed at or near the place of application to the web of base material for application thereto without the step of unwinding stored strips from a multiple-ply storage roll. Such "in situ" formation of self-adhering elastic material is convenient because of the difficulty of storing the self-adhering material in multiple-ply rolls from which it can readily be unwound.

In the manufacture of disposable diapers and the like, the gatherable base material is conventionally polypropylene, usually of a thickness of from about 1 to 2 mils (e.g., 1 or 1½ mils) although other suitable thicknesses and any other suitable material may obviously be employed. Similarly, although any suitable self-adhering elastic material may be employed, the materials described in the aforementioned Bunnelle et al U.S. patents are commercially available and suitable and to that extent are preferred.

While the invention has been described in detail with respect to specific preferred embodiments thereof, it will be apparent that upon a reading and understanding of the foregoing other embodiments and modifications may occur to those skilled in the art, which modifications and embodiments are believed to be within the scope of the invention and the appended claims.

What is claimed is:

1. A method of securing one or more curved composite elastic strips to a gatherable base material to elasticize at least selected portions of the base material comprises:
   (a) applying tensioning forces to a first strip of elastic material to elongate it;
   (b) joining a second strip of less-elongated material to the elongated first strip in longitudinally extending, laterally off-set relationship thereto to form a tensioned composite strip of elastic material, the second strip being sufficiently laterally flexible and sufficiently resistant to compression to cause the composite strip to laterally curve upon release of the tensioning forces;

(c) releasing the tensioning forces on the composite strip whereby to allow it to laterally curve; and (d) securing the composite strip to the base material.

2. The method of claim 1 wherein the gatherable base material is a moving continuous web of material.

3. The method of claim 2 including securing the tensioned composite strip to the base material before releasing the tensioning forces on the composite strip to allow it to curve laterally by displacing base material adjacent thereto.

4. The method of claim 3 including applying the second strip to the first strip in a laterally off-set relation thereto such that not more than about three-quarters of the width of the first strip is overlaid by the second strip.

5. The method of claim 3 including applying the second strip to the first strip in a laterally off-set relation thereto such that from about one-fifth to not more than about three-fifths of the width of the first strip is overlaid by the second strip.

6. The method of claim 2 wherein the first strip is a self-adhering elastic material.

7. The method of claim 6 wherein the first and second strips comprise the same self-adhering elastic material.

8. The method of claim 3 including tensioning the first strip to impose thereon from about 100% to 400% elongation.

9. The method of claim 3 wherein the first strip comprises a self-adhering elastic material comprising (a) a block copolymeric material comprising at least one substantially amorphous, rubbery polymeric midblock and at least one glassy poly(vinylarene) endblock, (b) a midblock associating resin, and (c) an endblock associating resin.

10. The method of claim 9 wherein the gatherable base material is a polyolefin.

11. The method of claim 10 wherein the second strip comprises the same self-adhering elastic material as the first strip.

12. The method of claim 8 wherein the first and second strips comprise self-adhering elastic material and including securing the tensioned composite strip to the base material by adhering the second strip to the base material.

13. The method of claim 12 wherein the first and second strips comprise self-adhering elastic materials of the type whose strength of adherence to the base material is inversely proportional to the degree of elongation imposed on the strip during adherence to the base material.

14. The method of claim 3 including the preliminary step of forming strips of self-adhering elastic material in situ from at least one mass of source material and employing the freshly formed strips in the method.

15. The method of claim 3 including transversely cutting the web into discrete articles containing thereon one or more segments of the composite strip thereby releasing the tensioning forces of the one or more segments of composite strips.

16. The method of claim 3 including enhancing displaceability of the base material by configuring one or more portions thereof adjacent composite strips secured thereto to free such portions for movement by the laterally curving composite strips.

17. An article comprising a gatherable base material having one or more elasticized portions thereof provided by one or more curved composite elastic strips secured thereto, the composite strips comprising a first strip of elastic material having a second strip of material adhered thereto and made by the steps of:

(a) applying tensioning forces to a first strip of elastic material to elongate it;

(b) joining a second strip of less-elongated material to the elongated first strip in longitudinally extending, laterally off-set relationship thereto to form a tensioned composite strip of elastic material, the second strip being sufficiently laterally flexible and sufficiently resistant to compression to cause the composite strip to laterally curve upon release of the tensioning forces;

(c) releasing the tensioning forces on the composite strips whereby to allow it to laterally curve; and (d) securing the composite strip to the base material.

18. The article of claim 17 made by securing the tensioned composite strip to the base material before releasing the tensioning forces on the composite strip to allow it to curve in its plane by displacing base material adjacent thereto.

19. The article of claim 18 comprising a garment made by securing the tensioned composite strip to a moving continuous web of the base material and transversely cutting the base material to form the article.

20. The article of claim 18 wherein the base material is a polyolefin.

21. The article of claim 18 including one or more portions of the base material being configured adjacent to composite strips secured thereto to be free for movement by the lateral curving of the component strips.

22. The article of claim 18 wherein the second strip is laterally off-set relative to the first strip to which it is adhered so that not more than about three-quarters of the width of the first strip is overlaid by the second strip.

23. The article of claim 18 wherein the second strip is laterally off-set relative to the first strip to which it is adhered so that from about one-fifth to not more than about three-fifths of the width of the first strip is overlaid by the second strip.

24. The article of claim 17 wherein the first strip comprises a self-adhering elastic material comprising (a) a block copolymeric material comprising at least one substantially amorphous, rubbery polymeric midblock and at least one glassy poly(vinylarene) endblock, (b) a midblock associating resin, and (c) an endblock associating resin.

25. The article of claim 24 wherein the second strip comprises the same self-adhering elastic material as the first strip.

26. The article of claim 24 wherein the gatherable base material is polypropylene.

* * * * *